United States Patent [19]

Zanin

[11] Patent Number: 5,665,671
[45] Date of Patent: Sep. 9, 1997

[54] COMPOUND TO DEFEND PLANTS FROM VEGETAL PARASITES

[76] Inventor: Roberto Zanin, c/o Hydro Geo—48 Silo Way, Bloomfield, Conn. 06002

[21] Appl. No.: 504,835

[22] Filed: Jul. 20, 1995

[30] Foreign Application Priority Data

Jul. 21, 1994 [IT] Italy .................. TV94A0087

[51] Int. Cl.$^6$ ................ A01N 59/16; C07F 1/08
[52] U.S. Cl. ............ 504/117; 504/121; 556/114; 556/115
[58] Field of Search .................. 556/114, 115; 504/117, 121

[56] References Cited

U.S. PATENT DOCUMENTS 5,298,253  3/1994  LeFiles et al. .............. 424/409

OTHER PUBLICATIONS

Schnitzer, Proceedings International Symposium of Humic Substances Milan, Italy, 1986, REDA Publisher, pp. 15–29.

Primary Examiner—Porfirio Nazario-Gonzalez

[57] ABSTRACT

A compound for plant defense from parasites, including fungi and bacteria, utilizing lower concentrations of Cu than available Cu-based fungicides. Until now compounds with high Cu concentration have been used, which damage the environment. This compound instead, besides containing Cu in minimal concentration, has a greater stability, due to the particular bond formed between the principal constituents. The compound is thus very valuable in the defense of plants, because it makes possible reducing treatments and it minimizes environmental risks.

7 Claims, No Drawings

COMPOUND TO DEFEND PLANTS FROM VEGETAL PARASITES

CROSS-REFERENCE TO RELATED CASE

This same invention has been filed by the same inventor with the Italian Patent Office on Jul. 21, 1994, receiving filing no. TV94A000087. Its title literally translated is "Method and related product for plants' defense from vegetal parasites, such as: plasmopara viticola, uncinula necator, puccinia graminis, venturia inaequalis, taphrina deformans, coryneum beyerickii, alternaria solani, etc., etc."

BACKGROUND—FIELD OF INVENTION

This invention relates to plant defense from parasites, including fungi and bacteria, by means of copper compounds. Examples of plant diseases on which the invention is effective are: botrytis, plasmopara viticola, uncinula necator, cercospora beticola, venturia pirina, venturia inaequalis, clasterosporium carpophilum, coryneum beyerickii, alternaria solani, taphrina deformans, exoascus deformans, sclerotinia fructigena, puccinia graminis, gymnosporangium, phragmidium subcorticum, bacillus phytophorus, psedomonas solacearum.

BACKGROUND—DESCRIPTION OF PRIOR ART

It is renown that inorganic copper (Cu) compounds, such as Bordeaux mixture, are very effective fungicides. Even though more potent systemic fungicides have been developed, copper compounds are still widely used in agriculture for plant disease control, thanks to their broader spectrum effectiveness.

Unfortunately available compounds contain Cu in high concentration, up to 300 g/100 l of water depending on the need. It is also known that Cu-based compounds are hardly soluble and easily washable away; thus, to insure the desired effectiveness, often more fungicide than necessary is applied on the plant. Eventually washing off from the plant, and seeping through the ground, to which Cu is subject when applied with water-based solutions, or when it subsequently rains, results in the presence of metallic-Cu in agricultural soils, in concentration higher than acceptable levels.

OBJECTS AND ADVANTAGES

A. The present invention instead contains much lower levels of Cu, between 12 and 60 g/100 l of water depending on the need, without reducing its effectiveness against vegetal parasites. The high effectiveness of the compound derives from a particular combination that is established between the Cu metal and a solution containing humic acid (HA) and fulvic acid (FA) in appropriate proportions.

B. The elevated stability of the compound allows utilization in its preparation of a very low dosage of the Cu metal under consideration, with the advantage that derives: even in presence of strong washing away, the Cu ion is released to the soil only in very minimal quantity.

C. The addition of appropriate carrier substrate such as bentonite, to improve the adhesion of the compound described above to the plant, prolongs the time during which Cu is present on the plant, and therefore improves its effectiveness to fight off vegetal parasites.

FURTHER OBJECTS AND ADVANTAGES

Besides the above, there are other advantages that are added to this new invention, for instance:

D. Because the bond between HA and FA is very strong, the compound possesses an extraordinary resistance to biodegradability and to light;

E. The complex metal-fulvo-humate (Cu-FA-HA) can rapidly penetrate the spores, thereby decreasing the time elapsed before obtaining results;

F. Very small doses are sufficient to inhibit the growth of fungi;

G. It is absolutely not phytotoxic;

H. The long persistence of the compound on the plant allows to reduce the number of treatments.

SUMMARY OF INVENTION

A composition comprising a compound to defend plants from vegetal parasites, formed by a fulvo-humate salt of Cu (Cu-FA-HA), and a carrier. The composition is more effective, persists on the plant for longer time, and has lower impact on the environment than available Cu compounds such as Bordeaux mixture.

DESCRIPTION OF INVENTION

The composition comprises a compound made by combining a solution of HA and FA, with Cu extracted from copper-sulfate ($CuSO_4$), and a carrier such as bentonite. The formula is the following:

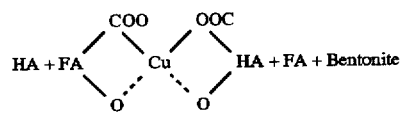

The combination between these substances takes place by reacting first the solution of HA and FA with Cu in water, then adding bentonite, and finally adding water to bring the solution up to volume; the following process steps and proportions are an example to obtain 100 g of compound:

1. From 0.1 g to 24 g of ($CuSO_4$) with 98% chemical purity, dissolved in water, to extract copper;
2. From 10 g to 30 g of a 21% solution of HA and FA, of which HA is 30% and FA is 70% of the total, are added;
3. From 5 g to 20 g of bentonite are added;
4. Water is then added to the mixture to obtain 100 g of composition.

The liquid composition obtained is then distributed on the plant through foliar application in dosage customarily used in agriculture for liquid products. A dilution ratio of 500 g of composition for 100 l of water is typical for application on most crops.

CONCLUSION

The stability of the Cu-fulvo-humate-salt derives from very strong bonds that are established between HA, FA and Cu, making the invented compound hardly soluble, thus giving out the Cu ion slowly during time. The addition of bentonite improves the adhesion of the compound to plants, therefore decreasing the need for repeated treatments. The effectiveness of the treatment against vegetal parasites is highly increased, and the impact on the environment is greatly minimized.

SCOPE OF INVENTION AND RAMIFICATIONS

The invention contains Cu in minimal concentration without losing effectiveness, and has more stability, due to the particular bond formed between the principal constituents. It obviates the drawbacks of commercially-available inorganic copper compounds to fight vegetal parasites. The compound becomes valuable in the defense of plants from vegetal parasites, because it makes possible a reduction of the treatments, and greatly diminishes impact on the environment.

Although the description above contains many specificities, these should not be construed as limiting the scope of the invention, but merely providing illustrations of some of the presently preferred features of this invention. In addition the invention description discusses mainly plant defense from fungi, but it is also effective on bacteria and other organisms affected by copper.

Thus the scope of the invention should be determined by the appended claims and their legal equivalents, rather than by the examples given.

I claim:

1. A compound to defend plants from parasites consisting essentially of copper, humic acid, and fulvic acid.

2. A method of obtaining the compound of claim 1 by extracting said copper from a solution of $(CuSO_4)$ and water, and subsequently adding a mixture of humic acid and fulvic acid.

3. The method of claim 2 wherein said $(CuSO_4)$ has 98% chemical purity.

4. The compound of claim 1 containing for 100 g of said compound an amount between 0.025 g and 6 g of copper, and an amount between 0.1 g and 3 g of humic acid and fulvic acid, wherein the relative content of fulvic acid ranges between 20% to 100% of the total of said amount of fulvic acid and humic acid.

5. A composition comprising a carrier and the compound of claim 1.

6. The composition of claim 5 comprising, for 100 g of said composition, up to 20 g of bentonite.

7. The compound of claim 1 where said parasites are fungi and/or bacteria.

* * * * *

UNITED STATES PATENT AND TRADEMARK OFFICE
CERTIFICATE OF CORRECTION

PATENT NO. : 5,665,671
DATED : September 9, 1997
INVENTOR(S) : Roberto Zanin

It is certified that error appears in the above-identified patent and that said Letters Patent is hereby corrected as shown below:

On the title page, item [73] should read --HydroGeo North America L.L.C. BloomField, CT--.

Signed and Sealed this

Tenth Day of February, 1998

Attest:

BRUCE LEHMAN

*Attesting Officer*  *Commissioner of Patents and Trademarks*